United States Patent
Casbi et al.

(10) Patent No.: US 9,726,909 B2
(45) Date of Patent: Aug. 8, 2017

(54) ADAPTIVE OPTICAL FILTER

(76) Inventors: Evelyne Casbi, Paris (FR); Jean-Paul Borreau, Paris (FR)

(*) Notice: Subject to any disclaimer, the term of this patent is extended or adjusted under 35 U.S.C. 154(b) by 701 days.

(21) Appl. No.: 14/119,429

(22) PCT Filed: May 25, 2012

(86) PCT No.: PCT/EP2012/059871
§ 371 (c)(1),
(2), (4) Date: Nov. 21, 2013

(87) PCT Pub. No.: WO2012/160196
PCT Pub. Date: Nov. 29, 2012

(65) Prior Publication Data
US 2014/0109302 A1    Apr. 24, 2014

(30) Foreign Application Priority Data

May 25, 2011 (FR) ...................... 11 54562

(51) Int. Cl.
*G02C 7/10* (2006.01)
*A61F 9/02* (2006.01)
(Continued)

(52) U.S. Cl.
CPC ............... *G02C 7/10* (2013.01); *A42B 3/226* (2013.01); *A61F 9/023* (2013.01); *G02C 7/101* (2013.01);
(Continued)

(58) Field of Classification Search
CPC .................................... G02C 7/101
See application file for complete search history.

(56) References Cited

U.S. PATENT DOCUMENTS 5,671,035 A * 9/1997 Barnes ............... G02C 7/101
                                                           351/158
6,070,264 A * 6/2000 Hamilton ........... A61F 9/067
                                                            2/8.8

FOREIGN PATENT DOCUMENTS

EP    0 341 519 A2    11/1989
EP    0 917 865 A1    5/1999
(Continued)

*Primary Examiner* — Phu Vu
(74) *Attorney, Agent, or Firm* — Blakely Sokoloff Taylor & Zafman LLP

(57) ABSTRACT

The invention relates to an optical filter comprising: at least one optically transparent liquid-crystal shutter, the shutter having a polarization voltage ULCD that marks a threshold between two polarization states, and being designed to switch between at least two opacities OP1 and OP2, OP2 being strictly higher than OP1, when it receives a voltage that is above or below, respectively, the polarization voltage ULCD; and an electronic system comprising: an electronic module for controlling the liquid-crystal shutter, designed to control the voltage applied to the liquid crystal shutter; a photosensitive sensor, designed to deliver, to the electronic control module, a continuous voltage Ucs that varies depending on the luminous intensity that it receives, the photosensitive sensor being the only power supply of the electronic control module and the liquid-crystal shutter, the optical filter being characterized in that, if the photosensitive sensor receives a luminous intensity below a dazzle threshold Ie, the liquid-crystal shutter has an opacity OP1, and in that the electronic control module is designed, when the photosensitive sensor receives a luminous intensity above the dazzle threshold Ie, to deliver, to the liquid-crystal shutter, a continuous voltage Ue that is strictly above the polarization voltage ULCD of the shutter, so that the latter switches from opacity OP1 to opacity OP2.

10 Claims, 6 Drawing Sheets

(51) Int. Cl.
*G02F 1/133* (2006.01)
*A42B 3/22* (2006.01)
*G02F 1/1335* (2006.01)

(52) U.S. Cl.
CPC ........ *G02F 1/1335* (2013.01); *G02F 1/13318* (2013.01)

(56) References Cited

FOREIGN PATENT DOCUMENTS

| FR | 2 373 808 A1 | 7/1978 |
| WO | WO 92/10130 A1 | 6/1992 |
| WO | WO 93/24858 A1 | 12/1993 |
| WO | WO 2008/148240 A1 | 12/2008 |
| WO | WO 2009/069166 A1 | 6/2009 |

\* cited by examiner

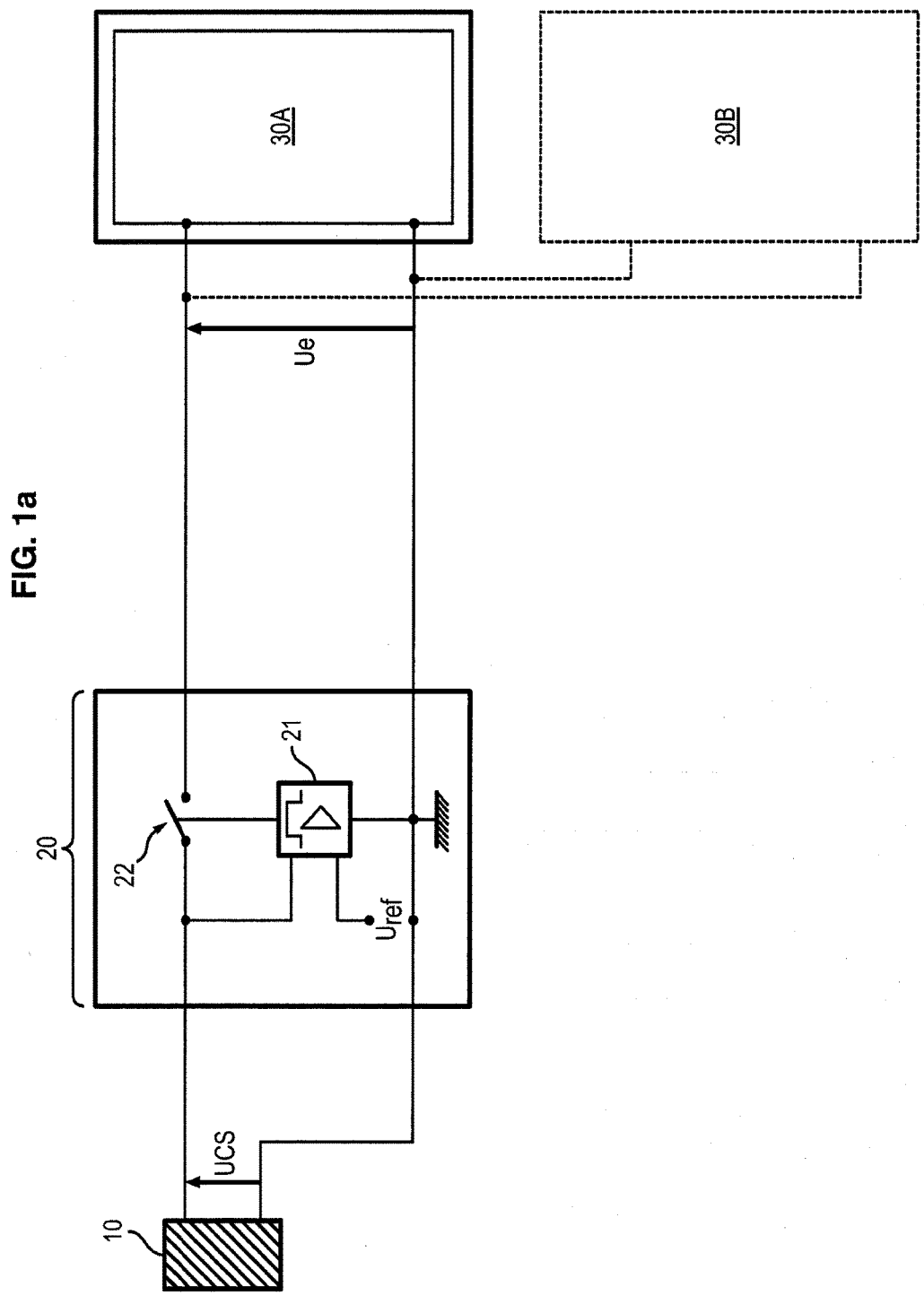

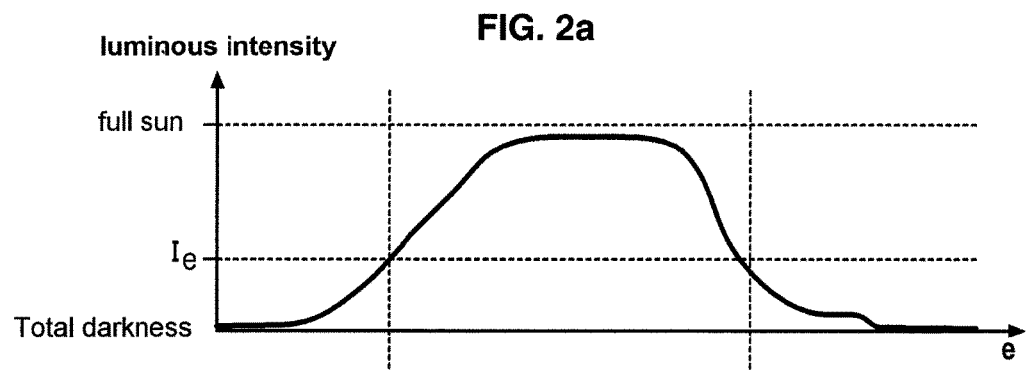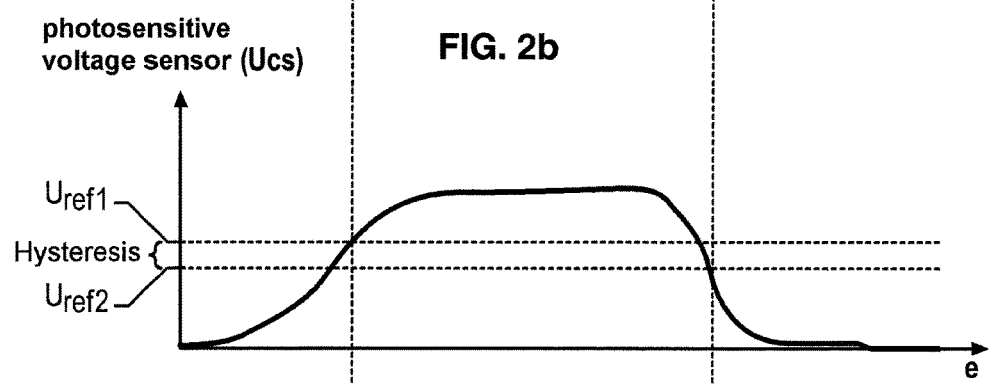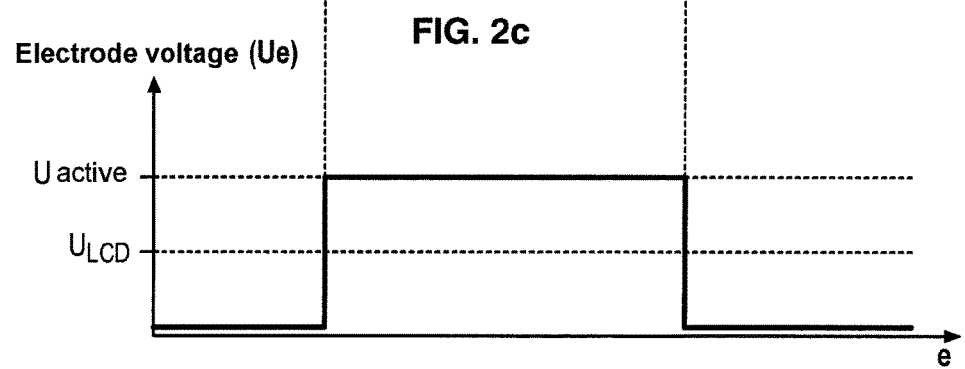

ADAPTIVE OPTICAL FILTER

FIELD OF THE INVENTION

The invention relates to the field of optical filters used to decrease luminous intensity, and more particularly the field of optical filters comprising crystal-liquid optical shutters which can adapt to ambient luminosity.

The invention can be implemented especially in devices for protection against light used daily as sunglasses.

PRIOR ART

Numerous devices for decreasing luminous intensity are already known, some of which comprise liquid-crystal shutters and can adapt to ambient luminosity.

Of particular interest is document FR 2,693,562 which describes sunglasses comprising a photosensitive sensor, transmitting a continuous signal, which is an increasing function of the luminous intensity which reaches it, and an electronic circuit connected to crystal-liquid screens, such that the transmittance of screens diminishes, that is, the opacity increases when the luminous intensity received by the photosensitive sensor increases.

Document FR 2,781,289 is also known and includes all the characteristics of document FR 2,693,562 and in which the darkening of the glasses is also proportional to the luminous intensity received by the photosensitive sensor.

Document PCT/US2007/019631 is also known, which proposes a solution in which a battery feeds an electronic control circuit of a liquid-crystal shutter. This electronic circuit is highly complex and therefore has a lengthy response time.

These devices however have numerous disadvantages.

First, the darkening of glasses of these devices requires an adaptation time of a few tens of seconds, or even a few seconds, which makes them poorly adapted to some situations during which darkening must occur instantaneously.

Examples of these situations especially are displacement situations in sunny weather, in a car or on a motorbike for example, during which the driver passes through tunnels, or under a canopy of trees, etc. Under normal circumstances, the driver can wear sunglasses or a helmet fitted with a tinted visor so as not to be dazzled. When he reaches one of these passages where rapid transitions of luminosity occur, the driver can remove his glasses or raise his visor, but this puts him in danger as this transition costs him a few seconds of inattention when he is not in possession of all his faculties.

Also, the driver is taking risks if he does not remove his glasses or its visor, as he then has reduced visibility.

None of the adaptable devices mentioned hereinabove resolves these problems because, over the abovementioned transition time, the user has perturbed or reduced visibility, which represents a risk both for him and for other users.

Also, for devices using liquid crystals, for example of nematic type, the feed of which is continuous, proposing darkening proportional to incident luminosity, it sometimes happens that the molecules of the liquid crystals do not align uniformly according to the orientation adapted to the required blocking. The result is optical phenomena such as variegations or sheens on the lenses of the glasses, which can be annoying for the user.

An alternative solution, presented in document WO 2009/069166, proposes an optical filter in which a photosensitive sensor delivers a voltage to a crystal-liquid screen to control blocking of the latter. The electronic circuit also comprises a resistor for rapidly discharging residual charges in the crystal-liquid screen so that the latter does not have the sheens mentioned hereinabove.

Also, solutions in which an extra battery outputs a voltage tailored to the shutter have been proposed, but there is still the risk that the battery fails the user.

As a consequence, an aim of the present invention is to provide an alternative to the previous solution, and in particular a secure optical filter for the user, allowing quasi-instantaneous adaptation to the incident luminous intensity on the filter, and avoiding any optical phenomenon awkward for the user.

Another aim of the invention is to be able to be easily used on a support such as glasses, a helmet, or even a window.

For this purpose, the invention proposes an optical filter comprising:

at least one optically transparent liquid-crystal shutter, having a polarisation voltage $U_{LCD}$ forming a threshold between two polarisation states, and adapted to switch between at least two opacities $OP_1$ and $OP_2$, $OP_2$ being strictly greater than $OP_1$, when the voltage which it receives is respectively less or greater than the polarisation voltage $U_{LCD}$ and an electronics system comprising an electronic control module of the liquid-crystal shutter, adapted to control the voltage of the liquid-crystal shutter, a photosensitive sensor adapted to deliver to the electronic control module a continuous voltage $U_{CS}$ variable as a function of the luminous intensity which it receives, the photosensitive sensor being the sole source of supply of the electronic control module and of the liquid-crystal shutter, and such that:

if the photosensitive sensor receives a luminous intensity less than a dazzle threshold $1_e$, the liquid-crystal shutter has an opacity $OP_1$, and the electronic control module is adapted, when the photosensitive sensor receives a luminous intensity greater than the dazzle threshold $1_e$, to deliver to the liquid-crystal shutter a continuous voltage $U_e$ strictly greater than the polarisation voltage $U_{LCD}$ of the shutter, such that the latter switches from the opacity $OP_1$ to the opacity $OP_2$.

Advantageously, but optionally, the optical filter proposed by the invention comprises at least one of the following characteristics:

when the photosensitive sensor receives a luminous intensity greater than the dazzle threshold $1_e$, the electronic control module delivers to the shutter a voltage $U_e$ greater than the polarisation voltage $U_{LCD}$ of the shutter to which some tens of volts are added, when the photosensitive sensor receives a luminous intensity less than the dazzle threshold $1_e$, the electronic control module delivers no voltage to the liquid-crystal shutter the electronic control module comprises a voltage comparator and an interrupter, the voltage comparator compares the voltage $U_{CS}$ delivered by the photosensitive sensor to a threshold voltage by excess $U_{ref1}$ or to a threshold voltage by default $U_{ref2}$, the voltages $U_{ref1}$ and $U_{ref2}$ being such that $U_{ref1}$ is greater than $U_{ref2}$ to which some tens of volts are added, and $U_{ref2}$ is greater than the polarisation voltage $U_{LCD}$ of the shutter to which some tens of volts are added, if the voltage $U_{CS}$ delivered by the sensor exceeds the threshold voltage by excess $U_{ref1}$, the interrupter closes and provides the liquid-crystal shutter with a voltage $U_e$ equal to the voltage $U_{CS}$, and the opacity of the liquid-crystal shutter becomes equal to $OP_2$, and if the voltage delivered by the photosensitive sensor $U_{CS}$ becomes less than the threshold voltage by default $U_{ref2}$, the interrupter opens, the liquid-crystal shutter ceases to be supplied and its opacity becomes equal to the opacity $OP_1$, the opacity $OP_2$ increases with the voltage $U_e$ at the terminals of the shutter, and the optical filter also comprises a voltage regulator, positioned downstream of the interrupter, and adapted to deliver a voltage $U_e$ which is constant and strictly greater than the polarisation voltage $U_{LCD}$ of the shutter, or else the opacity $OP_2$ is constant for all the voltage $U_e$ strictly greater than the polarisation voltage $U_{LCD}$, the optical filter also comprises a device for manual regulation of the opacity $OP_2$ of the liquid-crystal shutter, the optical filter also comprises a device of permanent manual deactivation of the electronic control module, the photosensitive sensor is integrated into at least one support surface, and the electronic control module is made on a printed circuit by silkscreen printing on at least one glass, the liquid-crystal shutter is integrated into a partial zone of a glass.

The invention also relates to a pair of glasses and a helmet equipped with the optical filter according to the invention.

DESCRIPTION OF FIGURES

Other characteristics, aims and advantages of the present invention will emerge from the following detailed description, with reference to the attached figures, given by way of non-limiting examples and in which:

FIGS. 1a and 1b represent two examples of electronic structures of an optical filter according to embodiments of the invention, FIGS. 2a to 2c represent examples of working diagrams of elements of the optical filter in relation to the incident luminous intensity on the filter, FIGS. 3a to 3c schematically represent examples of physical structures of an optical filter according to the invention.

DETAILED DESCRIPTION OF THE INVENTION

Figure 1B:
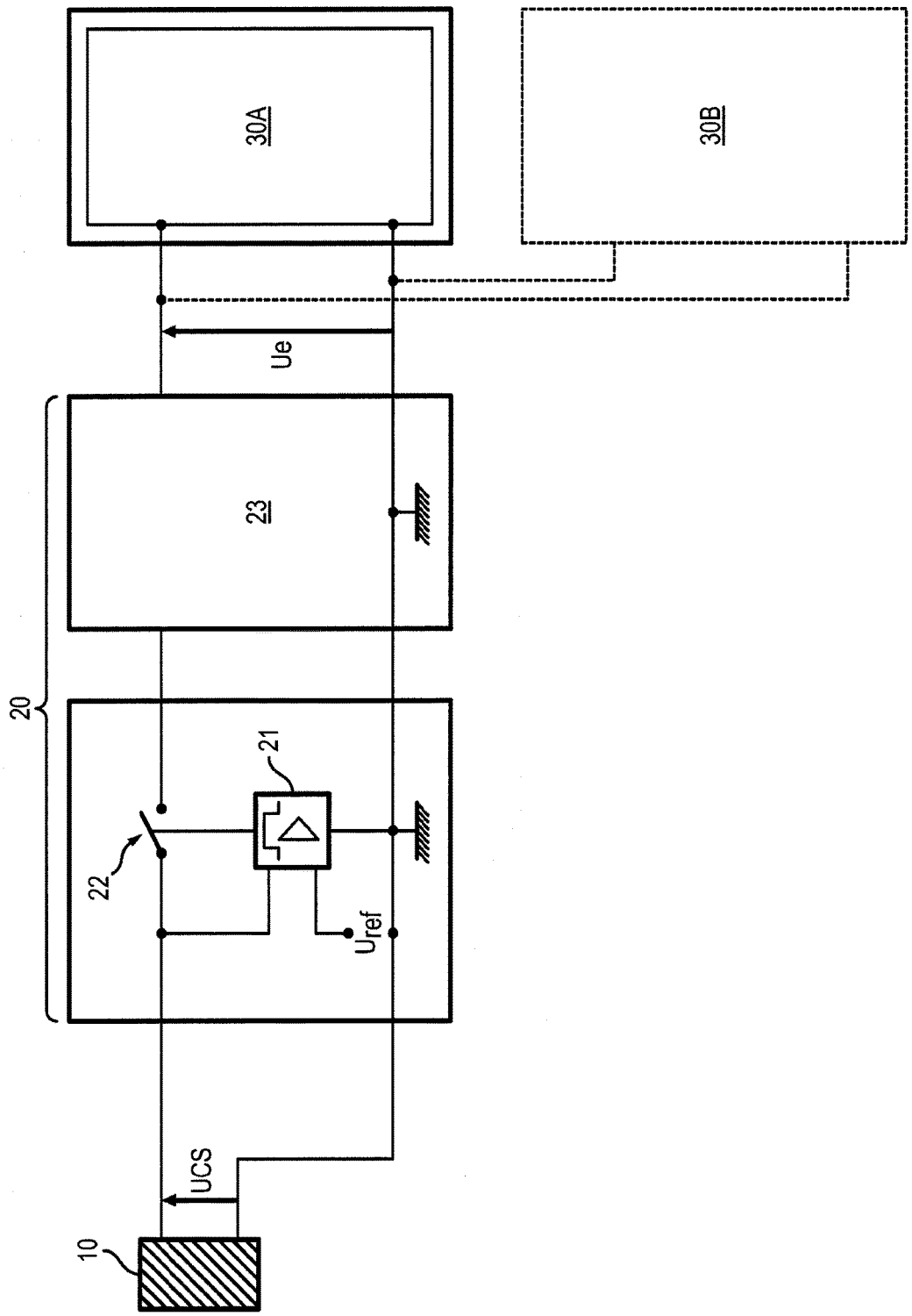

In reference to FIGS. 1a and 1b, these show examples of electronic structures according to preferred embodiments of the optical filter according to the present invention.

This optical filter 1 preferably comprises:

a photosensitive sensor 10, for example a photovoltaic cell, adapted to deliver a voltage $U_{CS}$ variable as a function of the luminous intensity which it receives. The voltage $U_{CS}$ can for example be continuous and increasing as a function of the luminous intensity received by the sensor 10, an electronic control module 20, at least one optical shutter 30, preferably crystal-liquid.

The optical shutter 30 is of type known from the state of the art. This is for example a liquid-crystal shutter of nematic type. Where appropriate, it preferably comprises electrodes 310, 311, a film of liquid crystals 32, optically transparent screens 330, 331 and polarisers 340, 341 (illustrated in FIG. 5).

Preferably, the film of liquid crystals 32 is positioned between two electrodes 310 and 311, with the latter in turn being positioned between two optically transparent screens 330 and 331.

Finally, the optical shutter 30 advantageously comprises two polarisers 340 and 341, the two polarisers being preferably positioned against the external surfaces of the optically transparent screens 330 and 331, such that the latter are located between the polarisers. Alternatively, the polarisers 340 and 341 can be between an electrode 310 (resp. 311) and a corresponding screen 330 (resp. 331), or between a corresponding electrode and the film of liquid crystals.

As is known to the expert, the two polarisers 340, 341 are typically oriented by 90° and the nematic molecules have a helicoidal orientation when no voltage is applied, allowing light to pass through without being blocked. The application of voltage to the terminals of these electrodes 310, 311 can cause, according to the value of the voltage, a particular orientation of the nematic molecules, causing partial or total clouding of the shutter 30. So, if the shutter 30 is placed on the path of an incident light beam, the quantity of light transmitted varies as a function of its opacity. In fact, the opacity is defined here as the inverse of transmittance, the latter being the ratio between the luminous intensity transmitted through the shutter and the incident luminous intensity. The opacity is therefore the ratio between the incident luminous intensity and the transmitted luminous intensity.

The optical shutter 30 preferably has a polarisation voltage $U_{LCD}$ forming a threshold between two distinct states, for which the opacity of the optical shutter has two different levels.

According to a preferred embodiment of the optical shutter, the polarisation voltage $U_{LCD}$ is such that, when it receives at its terminals a voltage less than this polarisation voltage, or even a zero voltage or an absence of voltage, the nematic molecules are oriented so as to give to the shutter a particular opacity, for example less than or equal to a first opacity $OP_1$. Preferably, for an input voltage to the terminals of the shutter 30 of less than $U_{LCD}$, the opacity of the shutter is constant and equal to the opacity $OP_1$. The opacity $OP_1$ is for example very low, that is, of the order of magnitude of the opacity of transparent glass traditionally used in the eyewear field.

Inversely, when the shutter 30 receives at its terminals a voltage greater than this polarisation voltage $U_{LCD}$, the nematic molecules are oriented so that the shutter has at least one opacity $OP_2$ strictly greater than the opacity $OP_1$.

According to a particular embodiment of the shutter, the latter can be a shutter of "all-or-nothing" type having an opacity $OP_1$ for an input voltage of less than the polarisation voltage $U_{LCD}$, or zero or for no voltage applied, and a constant opacity $OP_2$ strictly greater than the opacity $OP_1$ for an input voltage greater than the polarisation voltage $U_{LCD}$, According to an alternative embodiment, the liquid-crystal shutter 30 can have a variable opacity $OP_2$, for example increasing as a function of the input voltage at the terminals of the shutter 30.

According to the invention, the electronic control module 20 delivers a voltage $U_e$ to the terminals 31 of the electrodes 310, 311 of the shutter 30.

The electronic control module is itself electrically connected to the photosensitive sensor 10 which constitutes its sole source of supply. Therefore the photosensitive sensor 10 provides at output a voltage $U_{CS}$, this voltage being the input voltage at the terminals of the electronic control module 20.

The electronic control module 20 preferably comprises at least one comparator 21 and an interrupter 22. The comparator 21 receives the voltage $U_{CS}$ delivered by the photosensitive sensor 10 directly, and controls the opening and the closing of the interrupter 22, this interrupter being connected in series to the terminals of the electrodes 310, 311 of the optical shutter 30.

In this way, the sole source of supply of the optical shutter 30 is the photosensitive sensor 10. In particular, when the comparator 21 controls the opening of the interrupter 22, the shutter is not fed, and its opacity is therefore less than or equal to $OP_1$, and preferably equal to $OP_1$.

If the optical filter comprises a plurality of liquid-crystal shutters, they are connected in parallel on the output of the electronic control module 20 to receive at the terminals of their electrodes the same input voltage.

The operating principle of the optical filter consists of a threshold operation on the incident luminous intensity on the liquid-crystal shutters 30. If the luminous intensity exceeds a certain threshold, for example a dazzle threshold $l_e$, then the electronic control module 20 delivers to the shutter 30 a voltage strictly greater than the polarisation voltage $U_{LCD}$ so that the opacity of the shutter is equal to at least one opacity $OP_2$ strictly greater than the opacity $OP_1$.

A preferred embodiment of the invention is described hereinbelow.

In operation, the comparator 21 compares the voltage $U_{CS}$ delivered by the photosensitive sensor 10 to a threshold voltage $U_{ref}$. If the voltage $U_{CS}$ is strictly greater than the voltage $U_{ref}$, the comparator 21 controls the closing of the interrupter 22. So the voltage $U_e$ at the terminals 31 of the shutter or shutters 30 is equal to the voltage $U_{CS}$.

In the event where the voltage $U_{CS}$ is less than or equal to the voltage $U_{ref}$, the comparator 21 controls the opening of the interrupter 22, and the shutter 30 is no longer fed.

In reference to FIG. 1a, a particular embodiment of the electronic assembly of the optical filter 1 is shown.

In this embodiment, the voltage $U_e$ delivered to the liquid-crystal shutter 30 is equal to the voltage $U_{CS}$ when the interrupter 22 is closed. Now, in the case of a liquid-crystal shutter, for example of nematic type, there is a minimum polarisation voltage $U_{LCD}$ to be applied to the shutter so that the orientation of the molecules changes and darkening is effective on the glass.

Also, so that the orientation of the molecules of the liquid crystals changes entirely and evenly, the applied voltage must be greater than this polarisation voltage, with a few tens of volts added. In fact, if this is not the case, the molecules of the liquid crystals do not all orient uniformly, which is the origin of sheens or variegations which can appear on the glass and annoy the user.

Consequently, the voltage $U_{CS}$, which is transmitted to the shutters 30 when the interrupter 22 is closed, must be strictly greater than the polarisation voltage $U_{LCD}$, that is, equal to the polarisation voltage $U_{LCD}$, with a few tens of volts added, to be noted $U_{LCD}+\epsilon$. For this, the reference voltage $U_{ref}$ of the comparator is selected equal to $U_{LCD}+\epsilon$. For example, for a voltage $U_{LCD}$ of 3V, the voltage $U_{ref}$ is selected equal to 3.3V.

According to another embodiment of the invention, shown in FIG. 1b, the electronic control module also comprises a voltage regulator 23, positioned between the interrupter 22 and the shutter or optical-crystal shutters 30.

In the event where the opacity of the shutter 30 increases with the applied voltage, and particularly when the latter is greater than the polarisation voltage $U_{LCD}$, this voltage regulator 23 limits the value of the voltage $U_e$ at the terminals of the electrodes 310, 311 of the shutter 30 to limit clouding of the shutter. In fact, if the optical filter according to the invention is utilised for example in a form integrated into sunglasses lenses, it is preferable not to exceed an opacity threshold. If not, the user of the glasses would find this awkward or even could be put in danger.

According to an alternative embodiment of the invention such as illustrated in FIG. 1b, the voltage regulator 23 can be a voltage boost regulator. Therefore, the voltage $U_{ref}$ can be selected independently of the value of the voltage $U_{LCD}$. In particular, it can be selected less than the voltage $U_{LCD}$. In this case, the interrupter is closed for all voltage $U_{CS}$ greater than the voltage $U_{ref}$, which can comprise voltages less than $U_{LCD}+\epsilon$. The voltage regulator 23 therefore receives this voltage $U_{CS}$ and delivers at output a voltage $U_e$, preferably strictly greater than $U_{LCD}$, and even greater than or equal to $U_{LCD}+\epsilon$ so that the molecules of the liquid crystals can adopt uniform orientation.

In reference to FIG. 2, this shows working diagrams of the optical filter according to the invention.

The first diagram 2a illustrates a variation in the luminous intensity on a given time window. This luminous intensity varies from a state of total obscurity to a highly luminous state, similar to ambient luminosity in the sun, by crossing over a level $l_e$, which can be dazzling.

The second diagram 2b shows the voltage $U_{CS}$ delivered by the photosensitive sensor 10 over the evolution of the luminosity. The voltage $U_{CS}$ delivered as a function of the luminosity is adjusted by the manufacturer and it can be selected such that the voltage $U_{CS}$ delivered at the level of the dazzle threshold $l_e$ is strictly greater than the threshold voltage $U_{ref}$.

It is evident that the voltage $U_{CS}$ evolves at the same time as the luminous intensity.

Finally, the third diagram 2c illustrates the voltage at the electrodes 310, 311 of the liquid-crystal shutter 30. At the moment when the luminosity reaches the dazzling level $l_e$, the voltage $U_{CS}$ reaches the threshold greater than $U_{ref}$, as described hereinabove, and the transition to the level of the electrodes 310, 311 avoids the risk of sheen.

Again in FIG. 2b, it is clear that in reality the electronic control module 20 has hysteresis, causing the threshold voltage by excess to be different to the threshold voltage by default. These two voltages will be referred to as threshold $U_{ref1}$ and $U_{ref2}$ hereinbelow. This hysteresis stabilises the circuit. Electronic components ensuring a comparator function relative to two different thresholds respectively by excess and by default exist and are known to the expert. They will therefore not be described in greater detail hereinbelow.

In particular, according to the preferred embodiment for which the voltage $U_{CS}$ delivered by the photosensitive sensor 10 grows with luminous intensity, the activation voltage threshold when the luminous intensity exceeds the dazzling intensity $l_e$ is the maximal value of threshold voltages $U_{ref1}$ and $U_{ref2}$, and the deactivation threshold voltage when the luminous intensity becomes less than the dazzle threshold $l_e$ is the minimal value of the voltages $U_{ref1}$ and $U_{ref2}$.

For example, $U_{ref1}$ is strictly greater than $U_{ref2}$, and $U_{ref1}$ is the activation voltage threshold, and $U_{ref2}$ is the deactivation voltage threshold.

$U_{ref1}$ and $U_{ref2}$ are distinct by some tens of volts, and in particular they are selected preferably so that the polarisation voltage $U_{LCD}$ is strictly less than these two voltages. Here strictly means that $U_{ref2}$ is greater than $U_{LCD}$ with some tens of volts added, and $U_{ref1}$ is greater than $U_{ref2}$ with one ten or some tens of volts added.

Finally, the level of opacity $OP_2$ of the glasses, when the voltage $U_e$ at the terminals of the shutter 30 is greater than the polarisation voltage $U_{LCD}$, can be constant, and is defined originally by the equipment used, or a posteriori by the definition of the threshold voltage $U_{ref}$.

Alternatively, the optical filter can also comprise a manual control device of the opacity of the lenses to adjust the opacity $OP_2$ as a function of the wishes of users. For example, a voltage booster regulator can be used, whereof the output voltage is adjustable, to adjust the threshold voltage delivered to the liquid-crystal shutters.

The optical filter according to the invention can also comprise an additional device for manually deactivating and where appropriate manually reactivating the electronic control module.

This invention embodies numerous advantages.

First, the use of voltage thresholds avoids any risk of variegations associated with poor orientation of molecules in the liquid crystals, especially since these variegations are generally persistent, even if the voltage at the terminals of the liquid-crystal shutter again drops below the polarisation voltage.

Also, since the sole source of supply of the electronic control module and of the liquid-crystal shutter is the photosensitive sensor, the filter has no battery which could fail the user when he needs it. The operation of the filter is conditioned solely to the presence or not of sun or another light source.

This operation with threshold based solely on the output voltage of the photosensitive sensor allows quasi-instantaneous adaptation of the darkening of the lens. Quasi-instantaneous is understood as time of the order of one hundredth of a second, and which in particular is less than the persistence of vision time. This allows the user to perceive the adaptation as instantaneous, and even for sequences rapid change in luminosity, such as for example in some tunnels.

Finally, this extremely simple optical filter electronic circuit can be miniaturised and can be inserted very discretely into a cavity of a support 50.

Figure 3A:
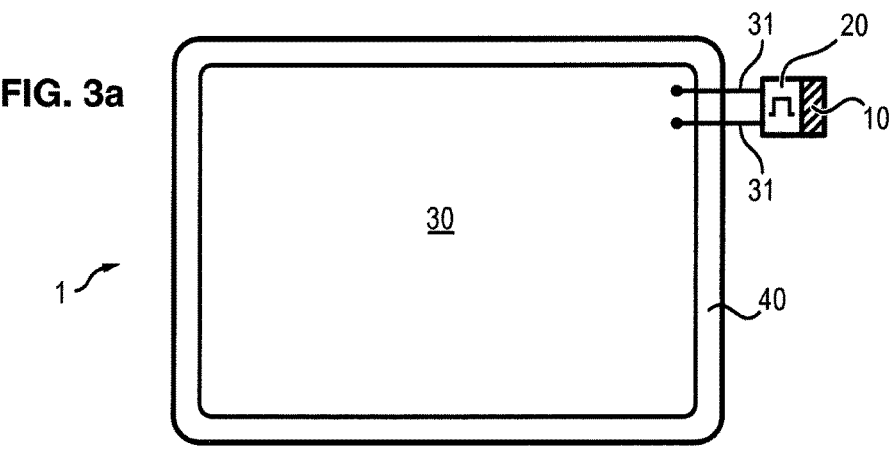

Whatever the support 50, two configurations are possible for integration of the optical filter 1 into the support. According to a first embodiment, and in reference to FIG. 3a, the photosensitive sensor 10 and the electronic control module 20 can be inserted into the support 50 (not shown in the figure), and be connected to the shutter 30 which can be integrated into a lens 40 via the electrodes 310, 311 and which is connected to the electronic module 20 via its terminals 31.

Figure 3B:
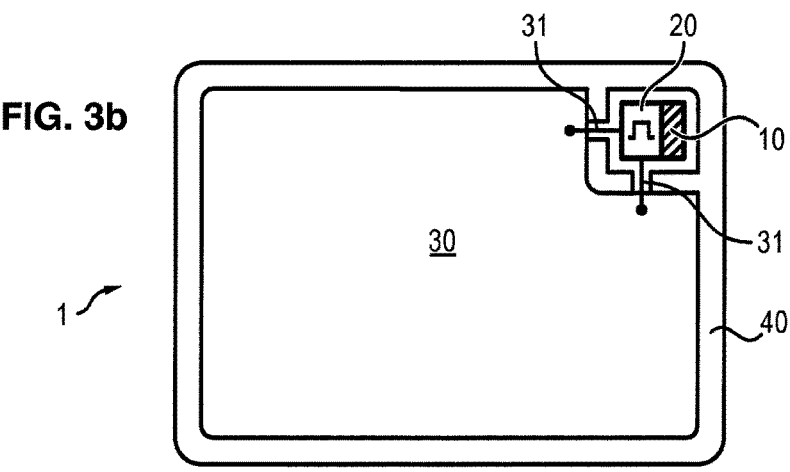
Figure 3C:
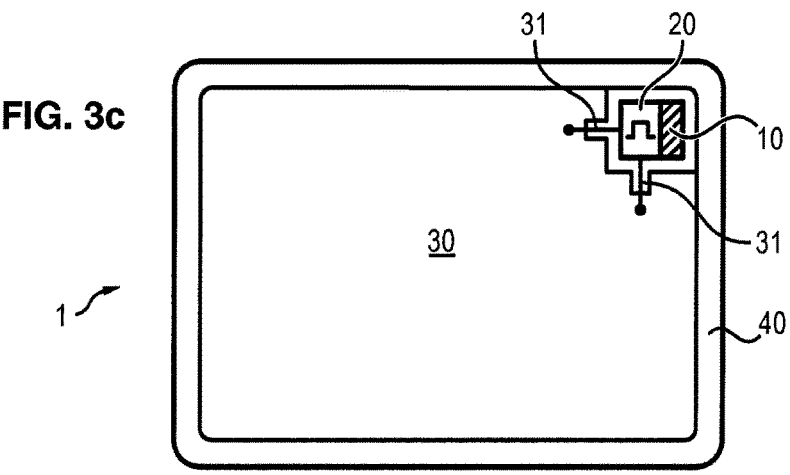

Alternatively, these days it is possible to use an optically transparent support surface made of glass or another material (for example some plastics) to integrate all the optical filter 1, as illustrated in FIGS. 3b and 3c.

In FIG. 3b, the photosensitive sensor 10 and the electronic control module 20 are integrated into a support surface 40 on which the shutter 30 is arranged without covering the photosensitive sensor 10 or the electronic control module 20.

In FIG. 3c, the photosensitive sensor 10 and the electronic control module 20 are placed on a support surface 40 or integrated into the latter, and are covered by the liquid-crystal shutter 30. Where appropriate, the optically transparent screens 330 and 331 of the optical shutter can form the lens 40 acting as support surface to the optical filter. Alternatively, a support surface 40 can be covered by the liquid-crystal shutter 30.

In these latter two cases, photosensitive sensors of photovoltaic cell type integrated into the lens are preferably used. Also, in this case the control electronics are preferably made in a printed circuit created by silkscreen printing on the glass.

Also in these cases, the liquid-crystal shutter 30 can cover only one part or some parts of the support surface 40.

Figure 4A:
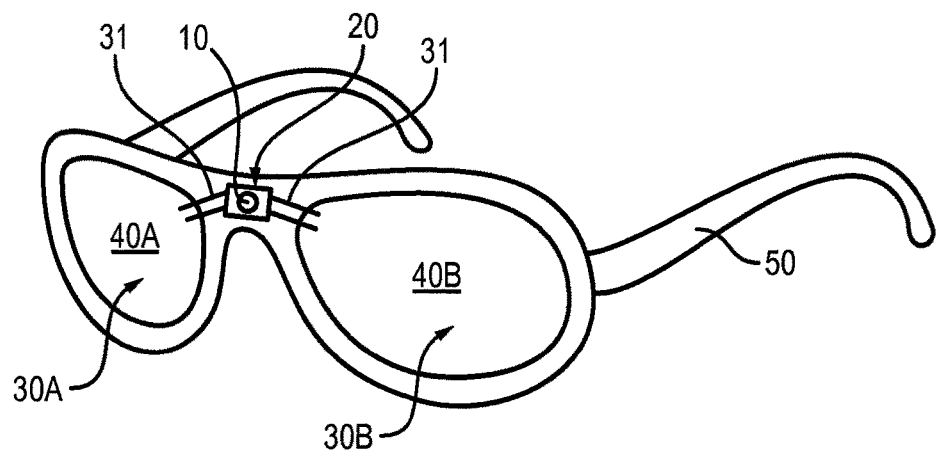
FIGS. 4a and 4b represent examples of integration of an optical filter according to the invention.

In reference to FIG. 4a, the support 50 can be a glasses mount comprising two lenses 40A and 40B forming the support surfaces 40 mentioned hereinabove. A photosensitive sensor 10 sufficiently small to be integrated very discretely in the mount 50 of the lenses can be used, as shown in the figure. Also, the electronic control module is simple enough to be miniaturised and also be integrated into the mount 50.

Also, the optical filter 1 comprises two liquid-crystal shutters 30A, 30B. The optically transparent screens 330A, 331A, 330B, 331B of the shutter 30 can constitute the lenses 40A, 40B of the glasses. Alternatively, at least one additional lens 41 can be adjoined to the shutters 30A, 30B so that the shutters 30A, 30B are integrated into the support surfaces 40 of the glasses.

Figure 5:
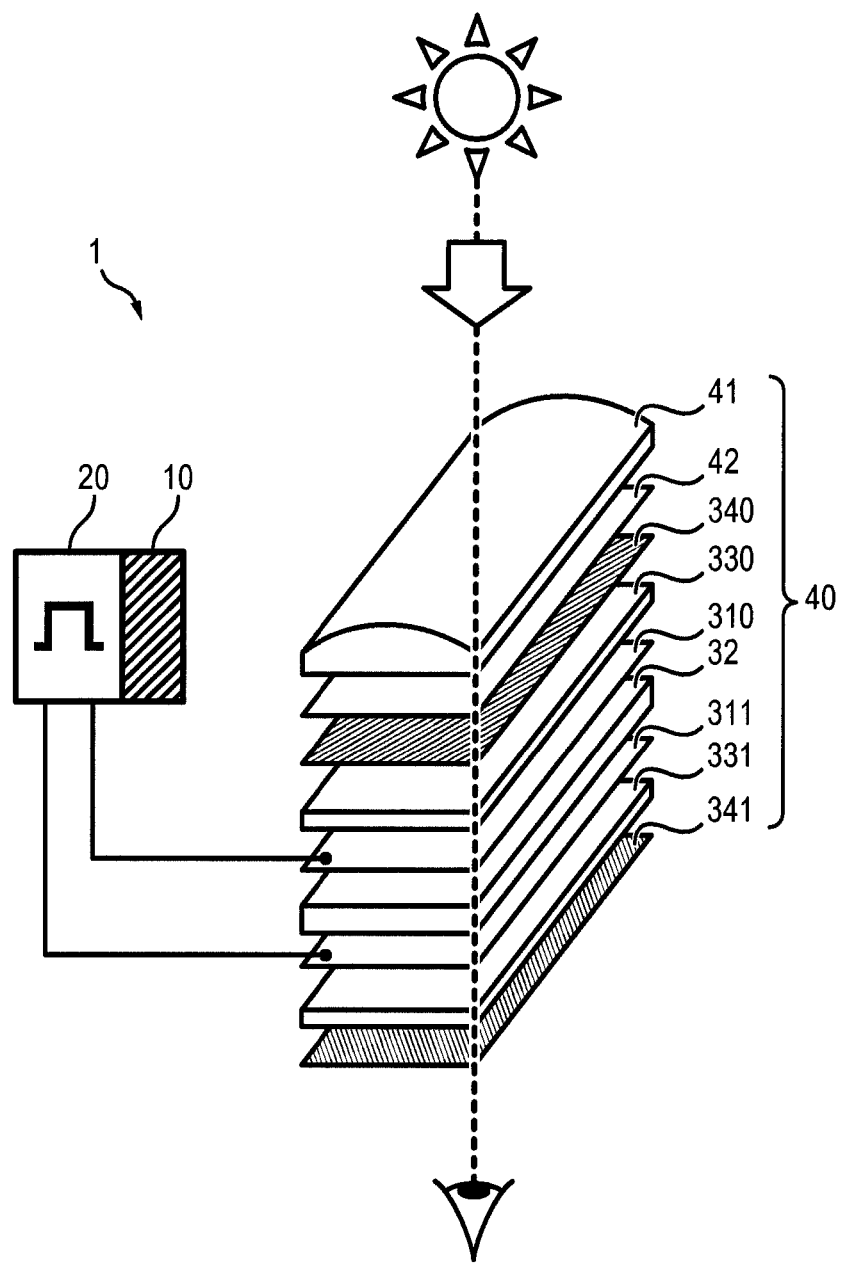
FIG. 5 represents an example of integration of an optical filter according to the invention in a spectacle lens with optical correction.

Also, integration of a liquid-crystal shutter 30 in glasses of lenses 40A, 40B can be combined with the fact that the glasses lend optical correction to the wearer.

Where appropriate, and in reference to FIG. 5, the additional glass 41 can be a glass slide worked according to known techniques to lend optical correction to the wearer, and placed upstream or optionally downstream of the shutter relative to the path of incident light.

Alternatively, the shutter is placed between two glass slides 41 machined to lend optical correction to the wearer, the shutters then being curved so as to join the contact surfaces of the glass slides.

Also, and again in reference to FIG. 5, the lenses 40 of the glasses can optionally comprise one or more anti-UV filters 42.

The invention applies similarly to the case of a monocle which has just one glass 40 and in this case the optical filter 1 comprises just a single liquid-crystal shutter 30 integrated into the lens.

The result is a unique product comprising a sun protection which deploys automatically as and when needed, and an optical correction, which is permanent. This unique product therefore eliminates any risk linked to rapid transition phases of luminous intensity mentioned hereinabove.

Figure 4B:
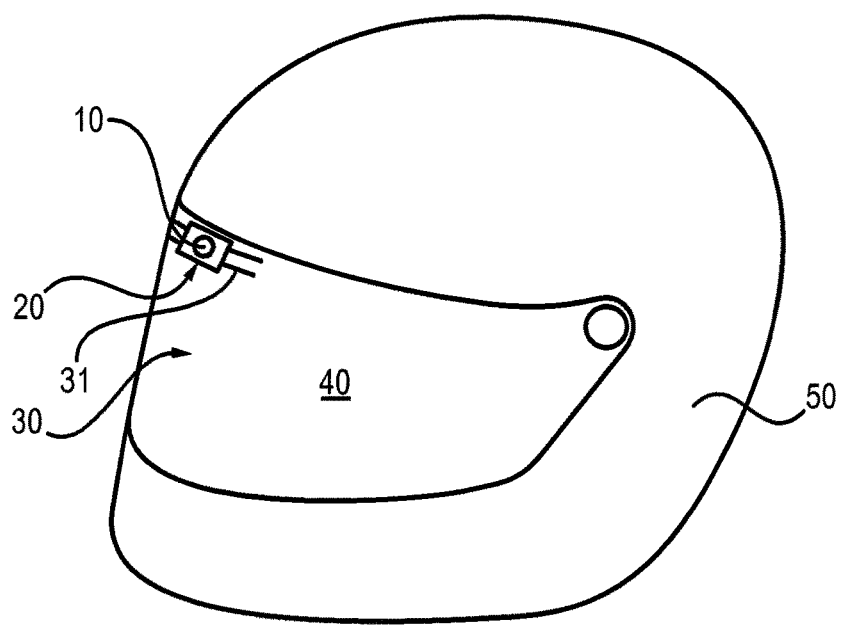

In reference to FIG. 4b, the support 51 can be a helmet, such as for example a helmet for two-wheeled vehicles, the helmet comprising a visor forming the lens 40 of the optical filter 1.

Also, the optically transparent screens 330, 331 are not limited to glass screens but can also be soft screens, for example made of soft plastic, so as to be able to deform to exhibit the preferred curvature.

The applications of the optical filter according to the invention are however not limited to this embodiment, but can also relate to window panes used in buildings, for example on windows, doors, or bay windows, or any type of vitreous surface whereof partial, temporary or permanent blocking can be realised by means of the optical filter according to the invention.

Irrespective of the application of the optical filter, the automatic character of its activation makes it more practical and of less risk to use than a traditional sun-protection device.

The invention claimed is:

1. An optical filter (1) comprising:
   at least one optically transparent liquid-crystal shutter (30), having a polarisation voltage $U_{LCD}$ forming a threshold between two states of polarisation, and adapted to switch between at least two opacities $OP_1$ and $OP_2$, $OP_2$ being strictly greater than $OP_1$, when the voltage which it receives is respectively less or greater than the polarisation voltage $U_{LCD}$ and
   an electronics system comprising
      an electronic control module (20) of the liquid-crystal shutter (30), adapted to control the voltage of the liquid-crystal shutter (30),
      a photosensitive sensor (10), adapted to provide the electronic control module (20) with a continuous voltage $U_{CS}$ variable as a function of the luminous intensity which it receives, the photosensitive sensor (10) being the sole source of supply of the electronic control module (20) and of the liquid-crystal shutter (30),
   the optical filter (1) being characterised in that
   the electronic control module (20) comprises a voltage comparator (21) and an interrupter (22), wherein the voltage comparator (21) compares the voltage $U_{CS}$ delivered by the photosensitive sensor (10) to a threshold voltage by excess $U_{ref1}$ or to a threshold voltage by default $U_{ref2}$, the voltage $U_{ref1}$ and $U_{ref2}$ being such that the threshold voltage by excess $U_{ref1}$ is greater than the threshold voltage by default $U_{ref2}$ with a few tens of volts added, and the threshold voltage by default $U_{ref2}$ is greater than the polarisation voltage $U_{LCD}$ of the shutter with a few tens of volts added
   when the optical filter comprises more than one optically transparent liquid-crystal shutters, all the optically transparent liquid-crystal shutters are connected in parallel at the output of the interrupter,
   the voltage comparator (21) controls the opening of the interrupter (22) when the voltage comparator detects that the voltage delivered by the photosensitive sensor (10) $U_{CS}$ becomes less than the threshold voltage by default $U_{ref2}$ when the photosensitive sensor (10) receives a luminous intensity less than a dazzle threshold $1_e$, so that the electronic control module (20) provides the liquid-crystal shutter (30) with no voltage and the liquid-crystal shutter (30) is no longer fed and liquid-crystal shutter (30) has an opacity $OP_1$, and
   the voltage comparator (21) controls the closing of the interrupter (22) when the voltage comparator detects that the voltage $U_{CS}$ delivered by the photosensitive sensor (10) exceeds the threshold voltage by excess $U_{ref1}$, when the photosensitive sensor (10) receives a luminous intensity greater than the dazzle threshold $1_e$, to provide the liquid-crystal shutter (30) through the interrupter with the continuous voltage issued by the photosensitive sensor $U_e$ strictly greater than the polarisation voltage $U_{LCD}$ of the shutter (30), such that the latter switches from the opacity $OP_1$ to the opacity $OP_2$.

2. The optical filter according to any one of claim 1, wherein the optical filter also comprising a voltage regulator (23), positioned downstream of the interrupter (22) between interrupter (22) and each liquid-crystal shutter, and adapted to limit the voltage applied to each liquid crystal shutter to a value $U_e$ which is constant and strictly greater than the polarisation voltage $U_{LCD}$ of the shutter (30).

3. The optical filter according to any one of claim 1, wherein the opacity $OP_2$ is constant for any voltage $U_e$ strictly greater than the polarisation voltage $U_{LCD}$.

4. The optical filter according to claim 3, also comprising a device for manual regulation of the opacity $OP_2$ of the liquid-crystal shutter (30).

5. The optical filter according to claim 1, also comprising a device for permanent manual deactivation of the electronic control module (20).

6. The optical filter according to claim 1, wherein the photosensitive sensor (10) is integrated into at least one support surface (330, 331, 40), and the electronic control module is made on a printed circuit by silkscreen printing on at least one lens (330, 331, 40).

7. The optical filter according to claim 1, wherein the liquid-crystal shutter (30) is integrated into a partial zone of a lens (40).

8. A pair of glasses comprising an optical filter according to claim 1, the optical filter comprising two liquid-crystal shutters (30A, 30B) adapted to form glasses or be integrated into the lenses (40A, 40B) of the glasses.

9. The pair of glasses according to claim 8, also comprising at least one glass (41) machined or processed so as to lend optical correction to a specific wearer.

10. A helmet comprising an optical filter according to claim 1, the liquid-crystal shutter (30) of the optical filter (1) being adapted to form or be integrated into a visor (40) of the helmet.

* * * * *